United States Patent
Sun

(10) Patent No.: US 8,684,001 B2
(45) Date of Patent: *Apr. 1, 2014

(54) APPARATUS FOR PROVIDING POSITIVE AIRWAY PRESSURE TO A PATIENT

(75) Inventor: Jianguo Sun, Redwood City, CA (US)

(73) Assignee: Curative (Beijing) Medical Technology Co. Ltd., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/601,148

(22) Filed: Aug. 31, 2012

(65) Prior Publication Data

US 2012/0325212 A1    Dec. 27, 2012

Related U.S. Application Data

(63) Continuation of application No. 12/094,876, filed as application No. PCT/US2006/061224 on Nov. 22, 2006, now Pat. No. 8,256,417.

(60) Provisional application No. 60/739,501, filed on Nov. 23, 2005.

(51) Int. Cl.
*A61M 16/00* (2006.01)

(52) U.S. Cl.
USPC .............................. 128/204.23; 128/204.18

(58) Field of Classification Search
USPC ............. 128/204.18, 204.21, 204.22, 205.18, 128/205.24, 203.12, 203.16, 205.14
See application file for complete search history.

(56) References Cited

U.S. PATENT DOCUMENTS

| | | |
|---|---|---|
| 3,961,627 A | 6/1976 | Ernst et al. |
| 4,193,406 A | 3/1980 | Jinotti |
| 4,239,039 A | 12/1980 | Thompson |
| 4,391,271 A | 7/1983 | Blanco |
| 4,706,664 A | 11/1987 | Snook et al. |
| 4,773,411 A | 9/1988 | Downs |
| 4,932,402 A | 6/1990 | Snook et al. |
| 4,938,212 A | 7/1990 | Snook et al. |
| 4,957,107 A | 9/1990 | Sipin |
| 5,107,830 A | 4/1992 | Younes |
| 5,134,995 A | 8/1992 | Gruenke et al. |
| 5,148,802 A | 9/1992 | Sanders et al. |
| 5,161,525 A | 11/1992 | Kimm et al. |
| 5,183,038 A | 2/1993 | Hoffman et al. |
| 5,188,098 A | 2/1993 | Hoffman et al. |
| 5,239,995 A | 8/1993 | Estes et al. |
| 5,245,995 A | 9/1993 | Sullivan et al. |
| 5,259,373 A | 11/1993 | Gruenke et al. |

(Continued)

OTHER PUBLICATIONS

International Search Report and Written Opinion issued in related application PCT/US06/61224 filed Nov. 22, 2006 mailed on Oct. 3, 2007, 12 pages.

(Continued)

*Primary Examiner* — Stephen Crow
(74) *Attorney, Agent, or Firm* — Lathrop & Gage LLP

(57) ABSTRACT

Methods and apparatus for treatment of medical disorders such as obstructive sleep apnea and congestive heart failure are disclosed. A method involves delivering pressurized air, oxygen or other breathing gas to a patient during a respiratory cycle, where pressure of the air is decreased according to an expiratory unloading factor during expiration. The timing and magnitude of the pressure change may be fully automated and responsive to feedback from a motor load sensor, optionally in combination with a pressure sensor.

7 Claims, 11 Drawing Sheets

(56) References Cited

U.S. PATENT DOCUMENTS

| | | | |
|---|---|---|---|
| 5,313,937 | A | 5/1994 | Zdrojkowski |
| 5,335,654 | A | 8/1994 | Rapoport |
| 5,339,807 | A | 8/1994 | Carter |
| 5,353,788 | A | 10/1994 | Miles |
| 5,390,666 | A | 2/1995 | Kimm et al. |
| 5,507,282 | A | 4/1996 | Younes |
| 5,535,738 | A | 7/1996 | Estes et al. |
| 5,551,418 | A | 9/1996 | Estes et al. |
| 5,582,163 | A | 12/1996 | Bonassa |
| 5,592,935 | A | 1/1997 | Elstran et al. |
| 5,598,838 | A | 2/1997 | Servidio et al. |
| 5,645,053 | A | 7/1997 | Remmers et al. |
| 5,794,615 | A | 8/1998 | Estes |
| 5,797,393 | A | 8/1998 | Kohl |
| 5,810,759 | A | 9/1998 | Merz |
| 5,875,783 | A | 3/1999 | Kullik |
| 5,927,274 | A | 7/1999 | Servidio et al. |
| 5,931,163 | A | 8/1999 | Stegmann et al. |
| 5,934,274 | A | 8/1999 | Merrick et al. |
| 5,937,855 | A | 8/1999 | Zdrojkowski et al. |
| 5,988,166 | A | 11/1999 | Hayek |
| 6,105,575 | A | 8/2000 | Estes et al. |
| 6,182,658 | B1 | 2/2001 | Hayek |
| 6,209,540 | B1 | 4/2001 | Sugiura et al. |
| 6,609,517 | B1 | 8/2003 | Estes et al. |
| 6,694,976 | B1 | 2/2004 | Kamada et al. |
| 6,708,690 | B1 | 3/2004 | Hete et al. |
| 6,860,265 | B1 | 3/2005 | Emerson |
| 6,932,084 | B2 | 8/2005 | Estes et al. |
| 7,077,131 | B2 | 7/2006 | Hansen |
| 7,296,573 | B2 | 11/2007 | Estes et al. |
| 7,367,338 | B2 | 5/2008 | Baecke et al. |
| 7,487,778 | B2 | 2/2009 | Freitag et al. |
| 7,533,670 | B1 | 5/2009 | Freitag et al. |
| 7,588,033 | B2 | 9/2009 | Wondka |
| 7,594,508 | B2 | 9/2009 | Doyle |
| 7,631,642 | B2 | 12/2009 | Freitag et al. |
| 7,722,698 | B2 | 5/2010 | Thompson et al. |
| 7,823,588 | B2 | 11/2010 | Hansen |
| 7,926,486 | B2 | 4/2011 | Childers |
| 8,075,676 | B2 | 12/2011 | Thompson et al. |
| 8,256,417 | B2 | 9/2012 | Sun |
| 2003/0015200 | A1 | 1/2003 | Hansen |
| 2005/0121033 | A1 | 6/2005 | Starr et al. |
| 2005/0247315 | A1 | 11/2005 | Estes et al. |
| 2007/0227540 | A1* | 10/2007 | Ljungberg et al. ....... 128/205.24 |
| 2009/0301488 | A1 | 12/2009 | |

OTHER PUBLICATIONS

Select file history from related U.S. Appl. No. 12/094,876 dated Sep. 15, 2011 through May 31, 2012, 62 pages.

* cited by examiner

APPARATUS FOR PROVIDING POSITIVE AIRWAY PRESSURE TO A PATIENT

RELATED APPLICATIONS

This application is a continuation of U.S. patent application Ser. No. 12/094,876, filed Jun. 4, 2012 which is a U.S. National Phase Application filed from PCT/US2006/061224, filed Nov. 22, 2006 which claims priority of U.S. Provisional Patent Application No. 60/739,501, filed Nov. 23, 2005. These applications are incorporated herein by reference.

BACKGROUND

Obstructive Sleep Apnea (OSA) is a breathing disorder that affects millions of patients having airways that are prone to narrowing and/or collapse during sleep. The obstruction of the airway can lead to decreased oxyhemoglobin saturation and increased levels of carbon dioxide, which are clinically associated with cardiovascular disease and death.

Continuous Positive Airway Pressure (CPAP) is an effective therapy for treating OSA. CPAP provides positive pressure to a patient's airway through a tube connecting an air flow generator to a patient interface, such as a mask, nasal cannulae, or tracheal device that is worn while the patient sleeps. The positive pressure prevents the airway from collapsing. It is estimated, however, that over 30% of OSA patients are not in compliance with their prescribed CPAP therapy because the mechanized breathing can be uncomfortable. In particular, the expiratory phase of CPAP respiration involves breathing against high pressure.

The main objective of CPAP therapy is to keep the airway open during inspiration, where the lungs are at lower pressure than the nose or mouth, and where negative pressure gradients and relaxed muscle may contribute to airway collapse. To achieve this end, traditional CPAP therapy provides a constant pressure level, i.e., the pressure required during inspiration. Thus the patient is required to exhale against high external pressure in the mask, cannulae or other device.

Bi-level positive airway pressure (bi-level PAP) therapies, such as those described in U.S. Pat. Nos. 5,239,995, 6,105,575, and 6,932,084, lower the applied pressure during exhalation. However, these bi-level therapies must detect the phase of patient breathing in order to switch between inspiratory pressure (high pressure) and expiratory pressure (low pressure). A delay in bi-level systems, which is present between detection of a change in respiratory cycle and adjustment of the airflow, could present a problem if the pressure at the end of an expiratory phase is too low to prevent airway collapse at the start of the next inspiration. For this reason, the average of the inspiratory and expiratory pressures of traditional bi-level therapy must be close to the CPAP level, i.e., the pressure required to maintain airway integrity. Bi-level therapy thus fails to offer an optimal treatment.

SUMMARY

Apparatus and methods are provided for delivering pressurized air to the airway of a patient for the treatment of OSA and other respiratory and/or pulmonary disorders.

In one embodiment, a method for providing positive airway pressure to a patient includes sensing load on a motor that pressurizes flow of air to an airway of the patient; comparing a pressure sensed proximate the airway to a therapeutic pressure, and adjusting motor speed, based on motor load, so that the sensed pressure equals the therapeutic pressure.

In one embodiment, an apparatus for providing positive airway pressure to a patient, includes a flow generator having a motor and a blower for providing a flow of air at a selected inspiratory pressure, and a patient interface connected with the flow generator, for conducting the air to an airway of the patient. A pressure sensor monitors pressure of the air at the interface and generates an interface pressure signal. A load sensor senses load on the motor and generates a load signal. A respiratory phase detector, in communication with the load and pressure sensors, processes the load signal with the interface pressure signal to determine a respiratory phase, and generates a phase signal. A processor in communication with the pressure sensor, load sensor and phase detector processes the phase, load and pressure signals with the inspiratory pressure and a selected expiratory pressure, to determine an expiratory unloading factor. The expiratory unloading factor indicates a difference in motor load required to generate the inspiratory and expiratory pressures at the interface. A pressure controller in communication with the processor and the flow generator alters operation of the motor during an expiratory phase and according to the expiratory unloading factor, to achieve the expiratory pressure at the interface.

In one embodiment, a method of providing positive airway pressure to a patient, includes supplying a flow of air to an airway of a patient at a selected inspiratory pressure; determining an inspiratory phase of respiration; monitoring pressure of the air proximate the airway, and monitoring load on a motor generating the flow of air. The pressure proximate the airway, the load and the selected inspiratory pressure are processed with a selected expiratory pressure that is lower than the inspiratory pressure, to correlate the inspiratory pressure with an inspiratory motor load and the expiratory pressure with an expiratory motor load. An expiratory unloading factor that achieves the expiratory pressure proximate the airway is determined from the correlated pressures. An expiratory phase of breathing is determined, and the expiratory unloading factor is applied to reduce pressure proximate the airway from the inspiratory pressure to the expiratory pressure.

In one embodiment, a method for providing positive airway pressure to a patient includes sensing load on a motor that pressurizes flow of air to an airway of the patient; correlating the load with pressure at the airway, and adjusting motor speed, based on motor load, so that the correlated pressure equals a therapeutic pressure that maintains functionality of the airway.

In one embodiment, a software product has instructions, stored on computer-readable media, wherein the instructions, when executed by a computer, perform steps for delivering positive airway pressure to a patient, including: instructions for supplying a flow of air to an airway of a patient at an inspiratory pressure; instructions for monitoring load on a motor pressurizing the flow of air; instructions for processing data indicative of the inspiratory pressure with data indicative of the load, to correlate the inspiratory pressure with the load; instructions for determining, from the correlated pressure and load, an expiratory unloading factor that achieves a selected expiratory pressure at the airway; instructions for determining an expiratory phase of breathing, and instructions for controlling the motor with the expiratory unloading factor, to reduce pressure at the patient airway from the inspiratory pressure to the expiratory pressure.

In one embodiment, an apparatus for providing positive airway pressure to a patient has a positive airway pressure module in communication with a CPAP machine, for regulating pressure of air delivered to a patient during an expiratory phase of breathing. The module determines load on a CPAP machine motor and correlates the load with a therapeutic CPAP level delivered to the patient by the CPAP machine. Based upon the correlated load and a selected expiratory pressure, the module reduces the CPAP level delivered to the patient, during the expiratory phase, to the expiratory pressure.

In one embodiment, a method for providing positive airway pressure to a patient, includes sensing pressure of air delivered to a patient airway, during an inspiratory phase of breathing; sensing load on a motor pressurizing the air to the patient, during an expiratory phase of breathing, and automatically reducing speed of the motor according to the sensed load, to reduce pressure at the patient airway, wherein pressure during the expiratory phase is directly proportional to the motor load.

DETAILED DESCRIPTION OF THE DRAWINGS

Figure 1:
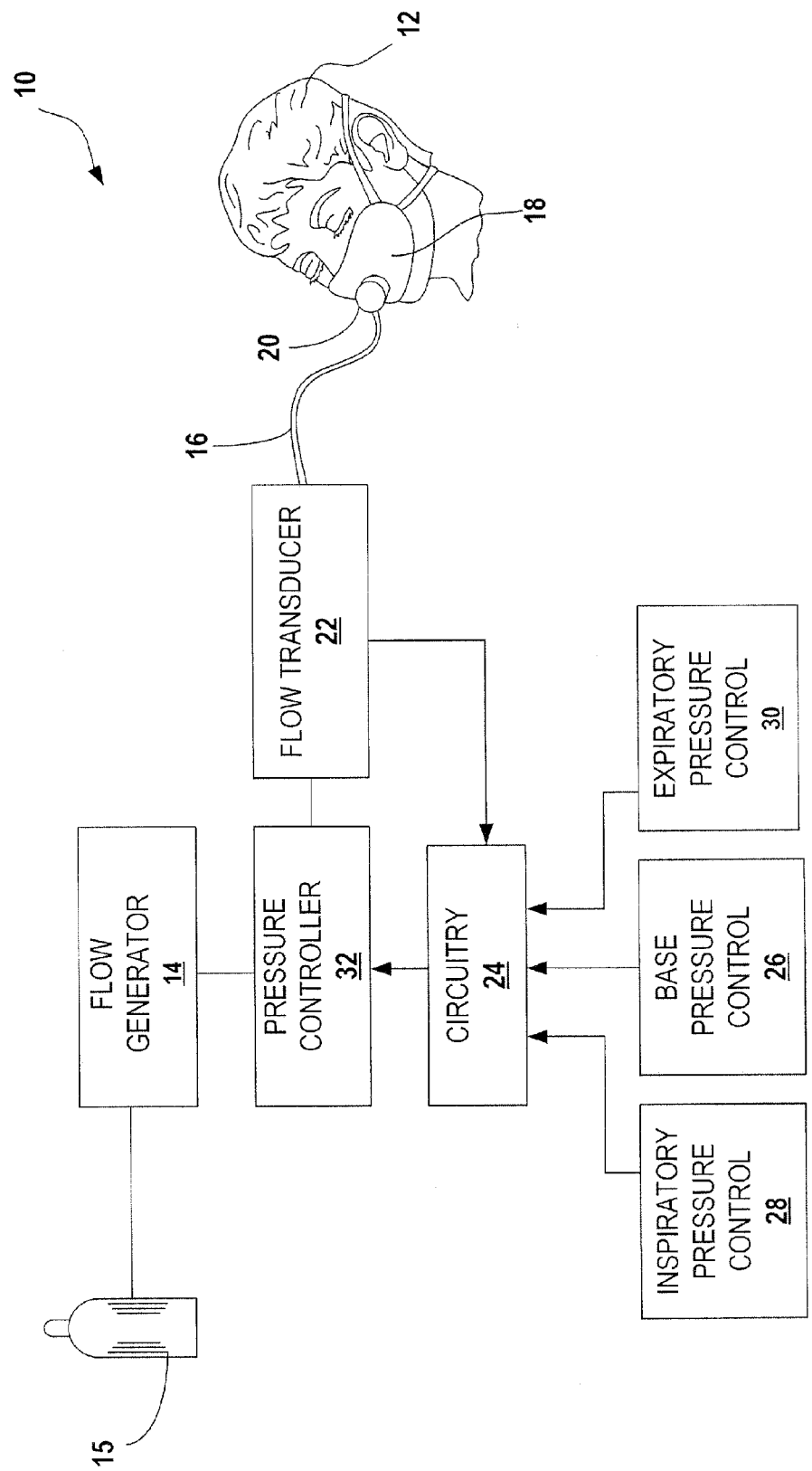
FIG. 1 is a block diagram of a prior art sleep apnea treatment apparatus.

FIG. 1 is a block diagram of a prior art sleep apnea treatment apparatus 10. Apparatus 10 delivers air to a patient 12 using an airflow generator 14, i.e., a conventional CPAP or bi-level PAP blower. Generator 14 may be a conventional CPAP or bi-level PAP blower that receives air, oxygen or other suitable breathing gas from a source 15, such as a pressurized bottle and/or the ambient atmosphere. Generator 14 delivers the air through tubing 16 to a patient interface, such as a mask 18. Mask 18 may include an exhaust port 20 for conducting exhaled air out of apparatus 10. A flow transducer 22 measures patient inspiration and expiration, and generates signals indicative of inspiration and expiration flow rates within tubing 16. Circuitry 24 receives signals from flow transducer 22 and additional controls 26, 28, 30. A base pressure control 26 establishes base pressure, which may correlate with the pressure necessary to maintain an open airway. An inspiratory pressure control 28 allows for setting a resistive gain to be applied to detected inspiratory flow, and an expiratory pressure control 30 permits setting of a resistive gain to be applied to detected expiratory flow.

Figure 2:
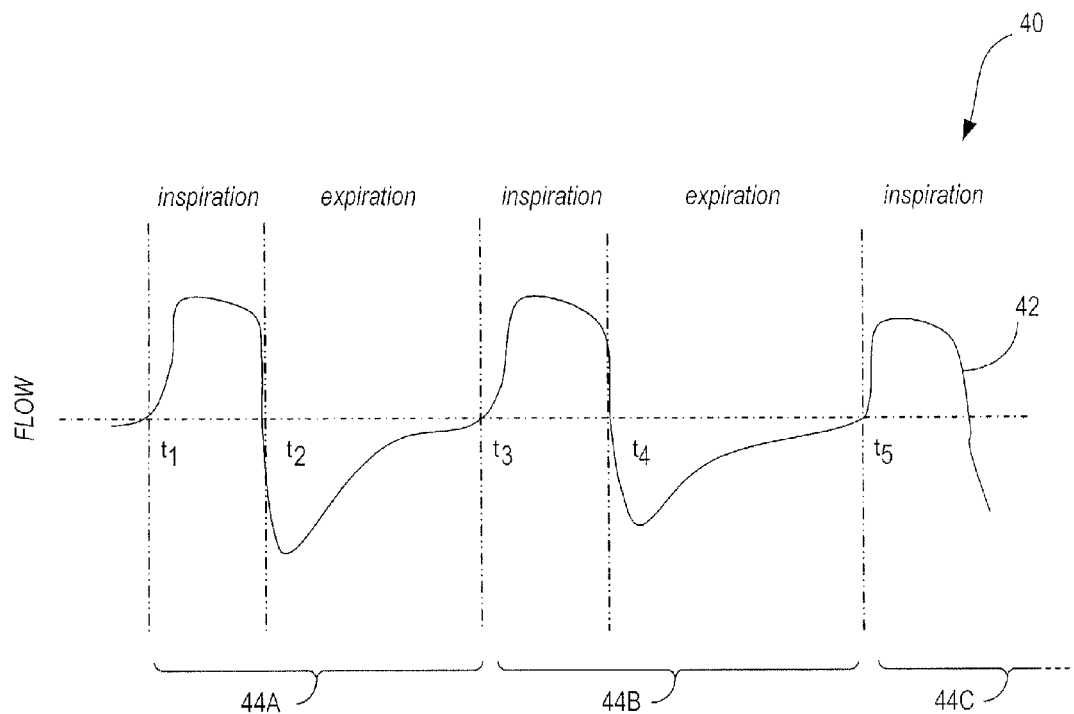
FIG. 2 is a graphical representation of a CPAP respiratory flow waveform.
Figure 3:
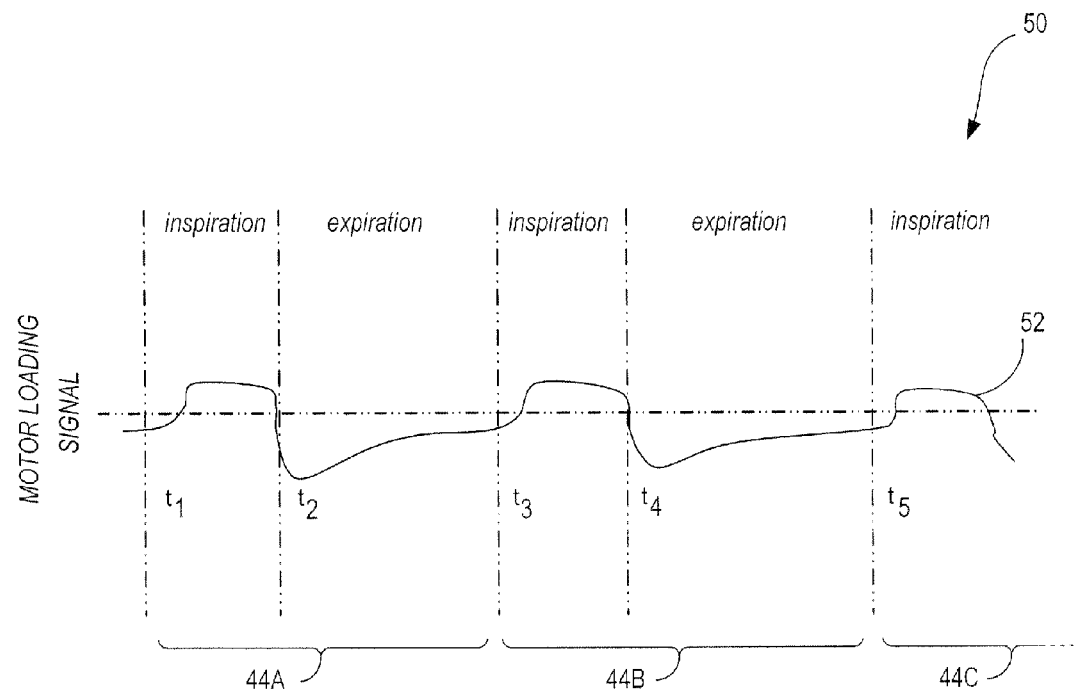
FIG. 3 is a graphical representation of load on a motor generating the CPAP respiratory flow waveform of FIG. 2.
Figure 4:
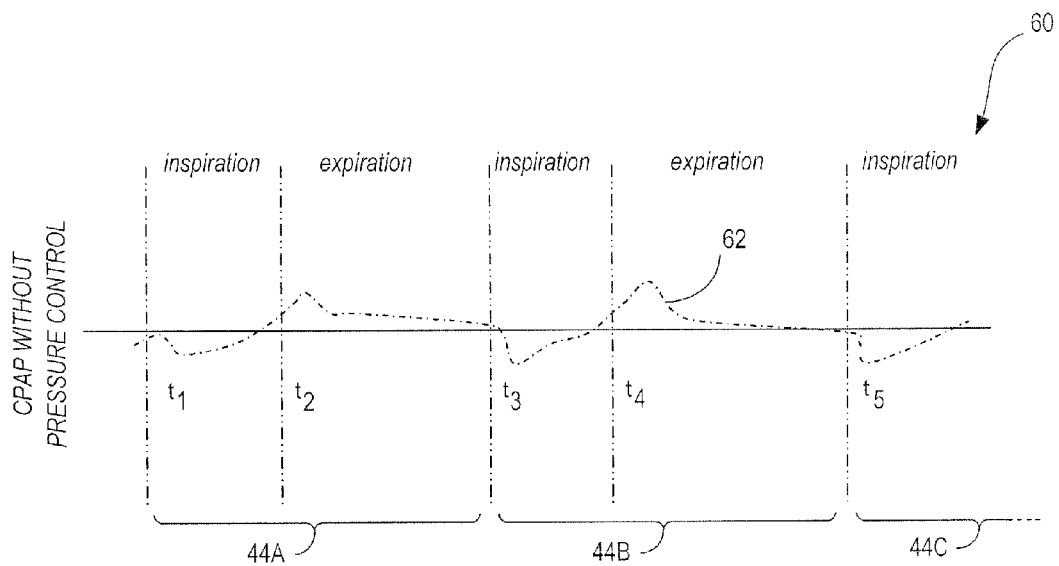
FIG. 4 is a graphical representation of a pressure waveform for CPAP without closed loop pressure control.

In response to output from circuitry 24, pressure controller 32 controls pressure of the air within tubing 16. Thus, the pressure of air delivered to the patient during an expiratory phase is a function of patient airflow rate. As shown in the graphs of FIGS. 2-4 and described below, controlling air pressure to the patient improves ventilation. However, pressure control based solely upon patient flow rate may lead to suboptimal ventilation, as it fails to account for load changes associated with elastic forces that are related to patient lung volume.

FIGS. 2 and 3 respectively illustrate (a) respiratory flow and (b) load variations on a motor (or generator, such as flow generator 14, FIG. 1) generating respiratory flow in CPAP or bi-level PAP therapy. Respiratory graph 40, FIG. 2, shows a respiratory flow waveform 42. Waveform 42 represents two and one half respiratory cycles 44A-44C, each respiratory cycle including an inspiration phase and an expiration phase. Graph 40 for example depicts the manner in which apparatus 10 delivers pressurized air to patient 12. As used herein, "air" refers to ambient air, oxygen or other suitable breathing gas obtained from the ambient atmosphere or from a bottle or tank. Inspiration appears as a positive flow where air (e.g., pressurized by a blower driven by the motor) enters a patient's respiratory system, e.g., between $t_1$ and $t_2$. Expiration appears as negative flow where air exits a patient's respiratory system and apparatus 10 through exhaust port 20, e.g., between $t_2$ and $t_3$.

Graph 50, shown in FIG. 3, shows changing motor load (e.g., work required of the motor) during respiratory cycles 44A-44C. During inspiration, for example from $t_1$-$t_2$, the load on the motor, represented by load signal line 52, increases. The power supplied to the motor increase to maintain the speed that produces a prescribed air pressure for preventing collapse of a patient's airway. Hereinafter, preventing collapse of a patient's airway may also be referred to as maintaining openness or functionality of the airway. During an expiratory phase (e.g., $t_2$-$t_3$), load on the motor decreases and less power is required to produce the prescribed air pressure.

Variations in motor load may affect the actual air pressure delivered to a patient. FIG. 4 shows a graph 60 of air pressure delivered to a patient in a CPAP system without closed loop pressure control. In graph 60, the power driving the motor is not adjusted according to the change of load. Therefore, the load increase during inspiration (see FIG. 3) causes air pressure, represented by line 62, to be delivered to the patient at a pressure that is lower than the set CPAP (or below prescribed therapeutic pressure). The opposite applies to the expiratory phase. Power to the motor is not adjusted as load on the motor is reduced during expiration (see FIG. 3 expiratory phases). The pressure delivered to the patient is thus increased (or higher than prescribed therapeutic pressure). High pressure during expiration may cause discomfort to the patient and discourage compliance with a prescribed CPAP or bi-level PAP regimen. Accordingly, pressure control may be provided in CPAP systems.

Figure 5:
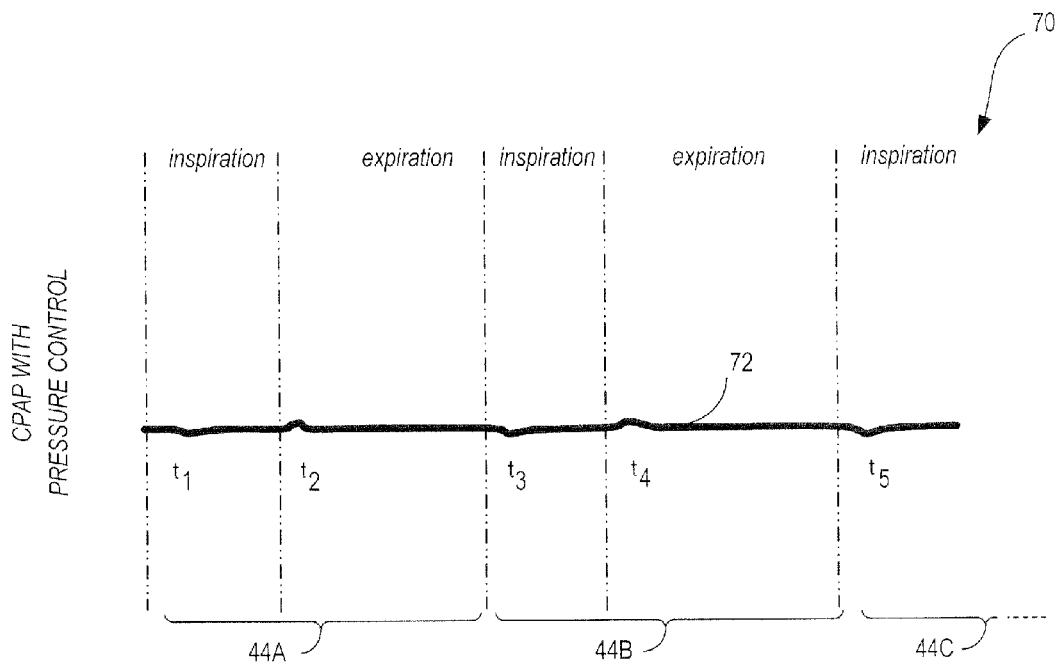
FIG. 5 is a graphical representation of a pressure waveform for CPAP with closed loop pressure control.

FIG. 5 is a graphical representation 70 showing a pressure waveform 72, as may result from a conventional CPAP system with closed loop pressure control. Air pressure at a patient's mask (or airway opening) may be sampled and monitored continuously, for example by a pressure transducer. A pressure control module, e.g., pressure controller 32, FIG. 1, compares set CPAP to actual pressure at the patient interface (e.g., a nasal mask such as mask 18) and adjusts power delivered to the motor according to pressure differences, to maintain a stable pressure at the patient interface. Inspiratory pressure does not fall below a therapeutic CPAP, as experienced with the system shown and described with respect to FIG. 4. However, neither does expiratory pressure drop below the CPAP. Hence, a patient undergoing therapy must exhale against substantial pressure, which may again lead to discomfort and non-compliance with CPAP therapy.

Figure 6:
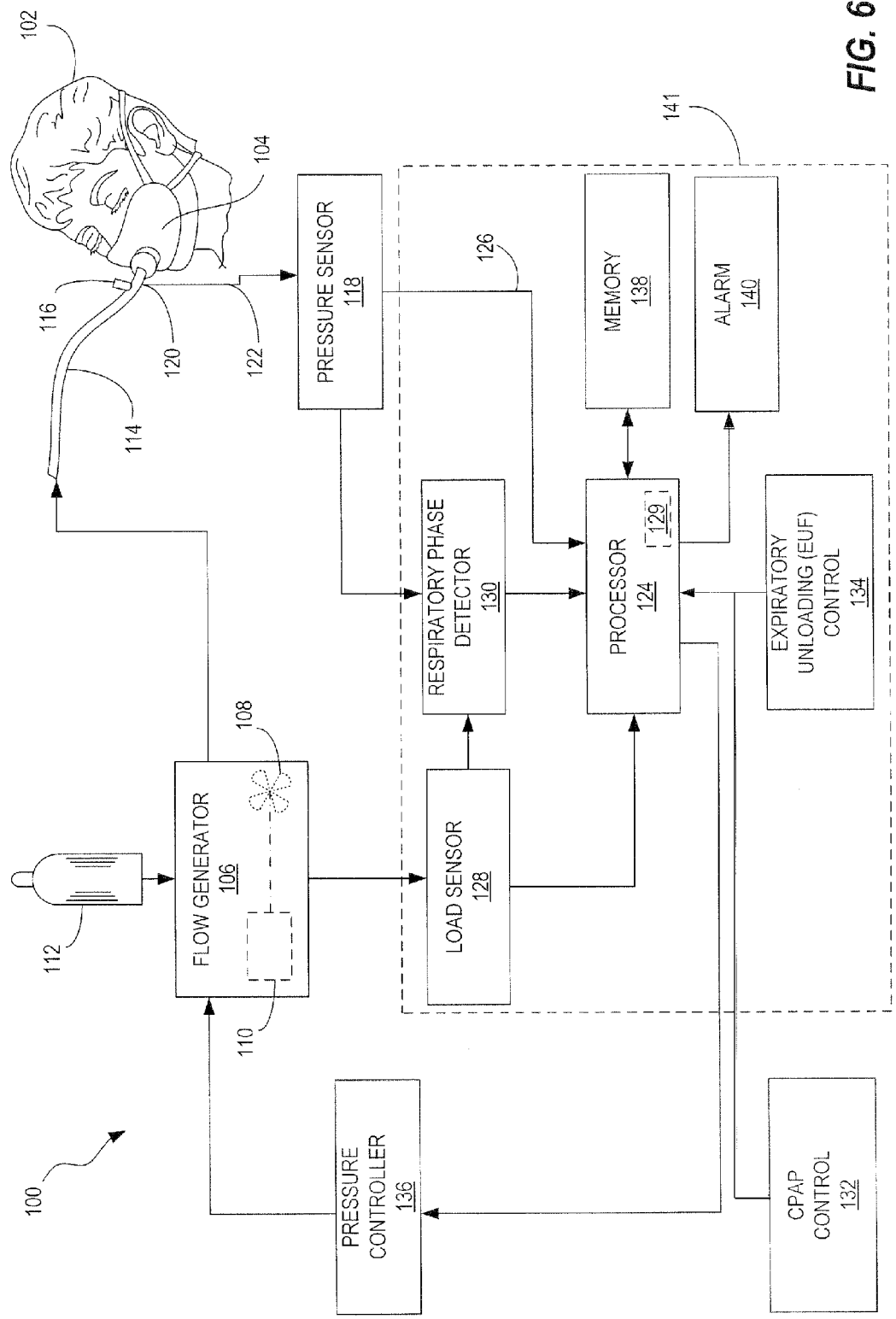
FIG. 6 is a block diagram of an apparatus for providing positive airway pressure to a patient, in accordance with an embodiment.

FIG. 6 shows an apparatus 100 that provides positive airway pressure to a patient. Apparatus 100 controls delivery of air to a patient 102, based not only upon pressure at a patient interface 104, but also based upon load on a motor. Apparatus 100 may thus compensate for changes in both resistive load, related to air pressure, and elastic load, which is related to patient lung volume.

Apparatus 100 includes an airflow generator 106, which may include an electro-mechanical valve and/or, as shown, a blower 108 and a motor 110. Airflow generator 106 receives air from source 112, such as a pressurized bottle, the ambient atmosphere or a combination thereof. Air is routed through tubing 114 from airflow generator 106 to patient interface 104. Patient interface 104 is for example a nasal or full face mask, a mouthpiece, a nasal seal, nasal prongs or cannulae, an endotracheal tube, a trachea adapter or any other suitable appliance for interfacing between a source 112 of air and a patient. Patient interface 104 includes an exhaust port 116 through which exhaled air may exit apparatus 100. Tubing 114 may be a large bore flexible tube made, for example, of Tygon® or polyvinylchloride (PVC).

A pressure sensor 118 monitors pressure of air at patient interface 104. Pressure sensor 118 may connect with a pressure pickup port 120 at patient interface 104 via a small tube 122, for example. Sensor 118 provides signals indicative of interface pressure to a processor 124; these signals may be produced wirelessly or by way of a wire 126, for example. Processor 124 is for example a microprocessor; an application-specific integrated circuit (ASIC) or intelligent circuitry may also or alternately be used with apparatus 100 in place of processor 124. Processor 124 likewise receives signals indicative of motor load, e.g., load on motor 110 of flow generator 106, from a load sensor 128. Load sensor 128 monitors motor 110 throughout the respiratory cycle to determine load on the motor during both inspiration and expiration. For example, during inspiration, load sensor 128 communicates a signal representative of increased load on motor 110 to processor 124; during expiration, load sensor 128 communicates a signal representative of decreased load on motor 110 to processor 124.

Processor 124 receives input from load sensor 128, pressure sensor 118 and a respiratory phase detector 130 that is also in communication with both pressure and load sensors 118, 128. Phase detector 130 determines breathing phase (inspiration or expiration) from pressure and load signals received from sensors 118, 128, respectively, and communicates the breathing phase to processor 124. A timer 129 provided with processor 124 may be used to determine average length and timing of inspiration and expiration phases. Timer 129 may further indicate the time of day, which may relate to a programmed start and/or stop time. Timer 129 may also be used to record start times, stop times and dates of use of apparatus 100, to aid in monitoring compliance with a prescribed treatment.

In one embodiment, pressure and load sensors 118, 128 continually monitor and communicate air pressure and load, respectively, so that timing of respiratory phases is not required. In this embodiment, processor 124 receives signals related to pressure and load from sensors 118, 128, along with breathing phase information from phase detector 130, and determines an air pressure to be provided to patient 102.

In one embodiment, a CPAP control 132 and an expiratory unloading control 134 communicate with processor 124. CPAP control 132 establishes an inspiratory pressure or base pressure, usually greater than zero, that is sufficient to maintain airway integrity, for example during an inspiration phase of the respiratory cycle. The CPAP level is typically a therapeutic pressure level for maintaining functionality of the airway, determined or selected by a medical professional, e.g., during a sleep study. Expiratory unloading control 134 permits selection of an expiratory unloading factor (EUF) that relates to a minimum target pressure during an expiratory phase of the respiratory cycle. A patient, or more typically a medical professional, may set the expiratory unloading factor to correspond with an expiratory pressure profile that is more comfortable for the patient and sufficient to maintain airway integrity during expiration.

Processor 124 calculates a required or desired air pressure based upon input from pressure sensor 118, load sensor 128, respiratory phase detector 130, CPAP control 132 and expiratory unloading control 134, and communicates the required or desired air pressure to a pressure control 136. Processor 124 for example directs pressure control 136 to control flow generator 106 by increasing, decreasing or maintaining speed of motor 110, to in turn control air pressure at patient interface 104. Pressure may likewise be controlled by use of an electro-mechanical valve. Pressure controller 136 is continuously governed by, and outputs variable air pressure responsive to, signals from processor 124. Pressure may be controlled according to a signal representative of patient interface pressure and/or motor load, along with an expiratory unloading factor (described below), so as to deliver the air to the patient at a therapeutic pressure during an inspiratory phase, where the therapeutic pressure is a pressure sufficient to counter airway collapse, and to deliver the air to the patient at a generally lower therapeutic pressure during an expiratory phase. A therapeutic pressure may be any pressure sufficient to prevent collapse of a patient's airway, with frequently used pressures between 2 to 20 cm $H_2O$, and more typically between 8 to 14 cm $H_2O$.

A memory 138 may be used to record pressure, load and respiratory phase data from pressure sensor 118, load sensor 128 and phase detector 130, along with data from timer 129, (where provided) and programmed parameters, e.g., CPAP and EUF.

In order to provide fail-safe operation, pressure controller 136 may receive input from CPAP control 132 and expiratory unloading control 134 via processor 124, to define an acceptable range of pressures that may be applied before a safeguard is activated. Optionally, the acceptable pressure range may be stored in memory 138 and provided to pressure controller 136 via processor 124. Safeguards activated upon breach of the acceptable pressure range may include automatic power cut-off or an audible/visual alarm 140. A minimum pressure will generally be a pressure sufficient to maintain airway integrity; a maximum pressure will be less than a pressure that may result in patient discomfort and/or damage to the patient's lungs. Collectively, processor 124, load sensor 128, phase detector 130, expiratory unloading control 134 and (optionally) alarm 140 may be referred to as a positive airway pressure module 141.

As described above, apparatus 100 may provide closed-loop or open-loop pressure control. In closed-loop control, pressure is for example lowered proportional to the motor's load when an expiratory phase commences. At the end of an expiratory phase, patient airflow and motor load are both close to zero. Pressure rises to the therapeutic inspiratory/CPAP level when an inspiratory phase starts. In open-loop control, pressure at the patient interface is lowered to a fixed, preset value (e.g., 3 cm $H_2O$ lower than inspiratory pressure) briefly and then ramped up to the inspiratory pressure before next inspiration phase starts. The duration of lowered pressure and pressure ramping may be determined based on individualized breathing patterns determined by monitoring a number of patient breathing cycles. For example, one or more expiratory phases may be monitored and a portion of the expiratory phase for applying a maximum expiratory unloading pressure estimated, e.g., from an average of the monitored phases. The maximum expiratory unloading pressure for example represents the highest pressure used to maintain functionality of the airway during expiration, without discomfort to the patient. After this maximum expiratory unloading portion of the expiratory phase has passed, pressure is ramped up from the maximum expiratory unloading pressure to the inspiratory/CPAP level, such that the inspiratory/CPAP level is supplied upon inspiration.

Figure 7:
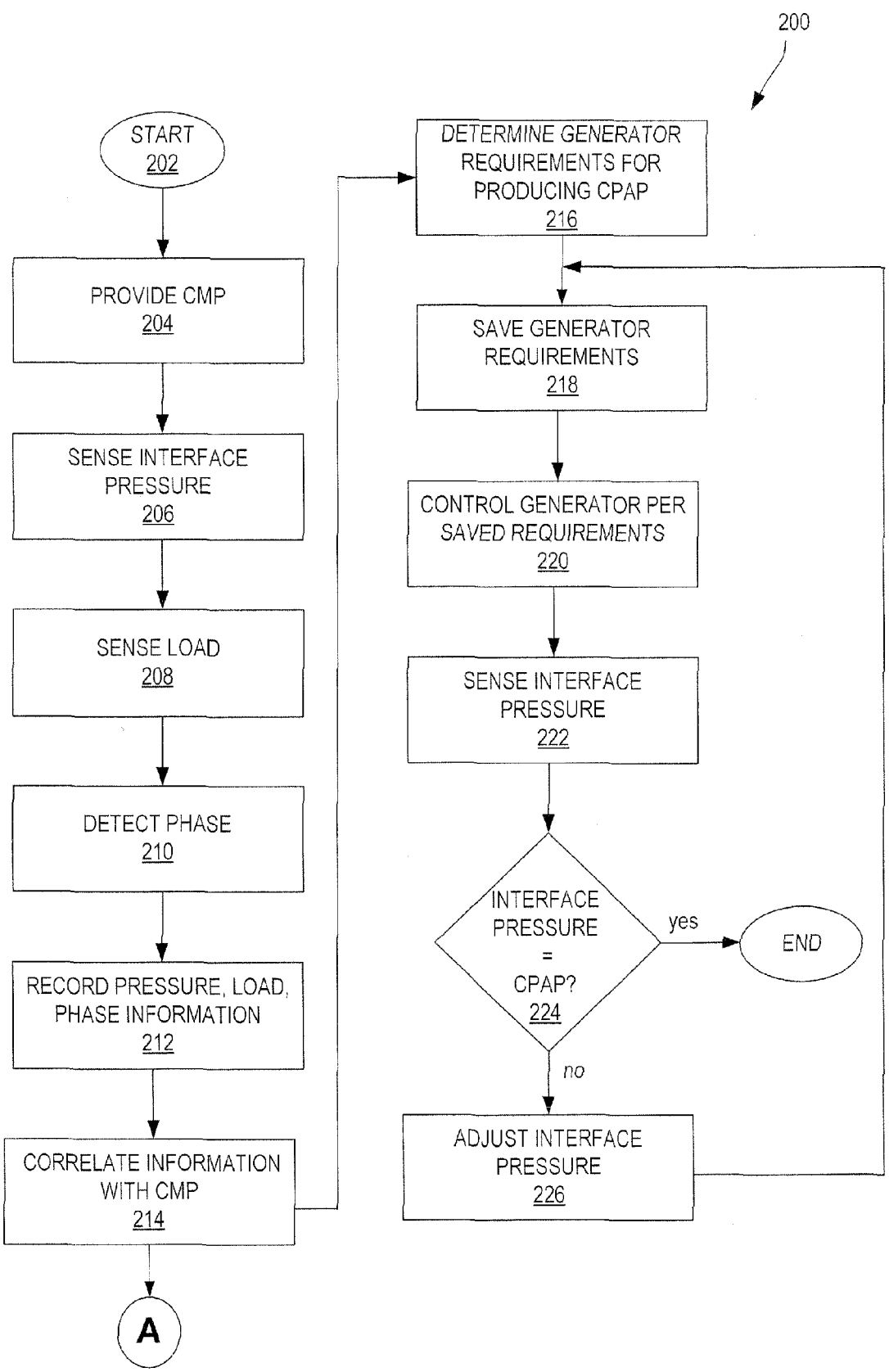
FIG. 7 is a flowchart showing one process for calibrating the apparatus of FIG. 6.

FIGS. 7-10 illustrate exemplary steps performed by an apparatus for providing positive airway pressure, such as apparatus 100. FIG. 7 shows a process 200 for calibrating apparatus 100. Following initiation in step 202, a constant minimal pressure (CMP), e.g., 5 cm $H_2O$, is applied, in step 204. The CMP for example corresponds with a prescribed CPAP level. In one example of steps 202, 204, apparatus 100 is turned on and a calibration mode is selected. Flow generator 106 provides air/breathing gas to patient interface 104, under control of pressure controller 136. The pressure at the patient interface is sensed, in step 206, and load on flow generator 106, or more particularly, motor 110, is measured, in step 208. Respiratory phase is detected in step 210, and pressure, load and phase are recorded in memory 138, in step 212. In one example of steps 206-212, pressure sensor 118 detects pressure at a pressure pickup port 120 in or near patient interface 104. Pressure sensor 118 generates a signal indicative of sensed air pressure and relays the signal to decision circuitry, e.g., processor 124. Processor 124 likewise receives a signal representative of load on motor 110, from load sensor 128. Respiratory phase detector 130 receives input from pressure sensor 118 and load sensor 128, to determine inspiration and expiration phases of patient breathing, and relays phase information to processor 124. Processor 124 communicates with memory 138 to save the pressure, load and phase information.

In step 214, processor 124 correlates the pressure, load and phase information with the CMP provided in step 204. Processor 124 processes the correlated parameters with a prescribed CPAP, e.g., 12 cm $H_2O$, to determine the requirements on flow generator 106/motor 110 to produce the CPAP at patient interface 104, in step 216. In one example of steps 214 and 216, processor 124 correlates the pressure and load information with inspiratory phase information and the constant minimal pressure. Obstruction of a patient's airway most frequently occurs during inspiration (when negative pressure gradients and relaxed muscle may lead to collapse of the airway). Therefore adequate CPAP levels are provided to a patient during inspiration. In step 218, generator requirements (e.g., motor speed) necessary to achieve the prescribed CPAP level are saved in memory.

In step 220, a flow generator is controlled as determined in step 216 to produce the prescribed CPAP level at the patient interface. Pressure at the patient interface is sensed in step 222. Step 224 is a decision. If sensed pressure corresponds with the prescribed CPAP, calibration process 200 ends. If sensed pressure does not match the CPAP, the flow generator is controlled to gradually adjust pressure at the patient interface until sensed pressure and CPAP are equal, in step 226. Process 200 continues by saving motor requirements, e.g., motor speed related to the achieved CPAP are recorded in memory, in step 218, and the saved motor requirements as verified in steps 220-224.

In one example of steps 220-226, pressure controller 136 increases the speed of motor 110 to a determined speed for achieving the 12 cm $H_2O$ CPAP at patient interface 104 (determined in calibration step 216). Pressure at pressure pickup port 120 is sensed with pressure sensor 118 and relayed to decision processor 124. If sensed pressure equals the 12 cm $H_2O$ prescription, calibration process 200 ends. However, if sensed pressure is less than 12 cm $H_2O$, motor 110 is sped up, under control of pressure controller 136, until feedback from sensor 118 indicates that pickup port pressure has risen to 12 cm $H_2O$. Conversely, if sensed pressure is greater than 12 cm $H_2O$, controller 136 decreases the speed of motor 110 until pickup port pressure falls to the prescribed CPAP. Once sensed pressure and CPAP are equal, speed of and/or load on motor 110 at the prescribed CPAP (at patient interface 104) are saved in memory 138.

Figure 8:
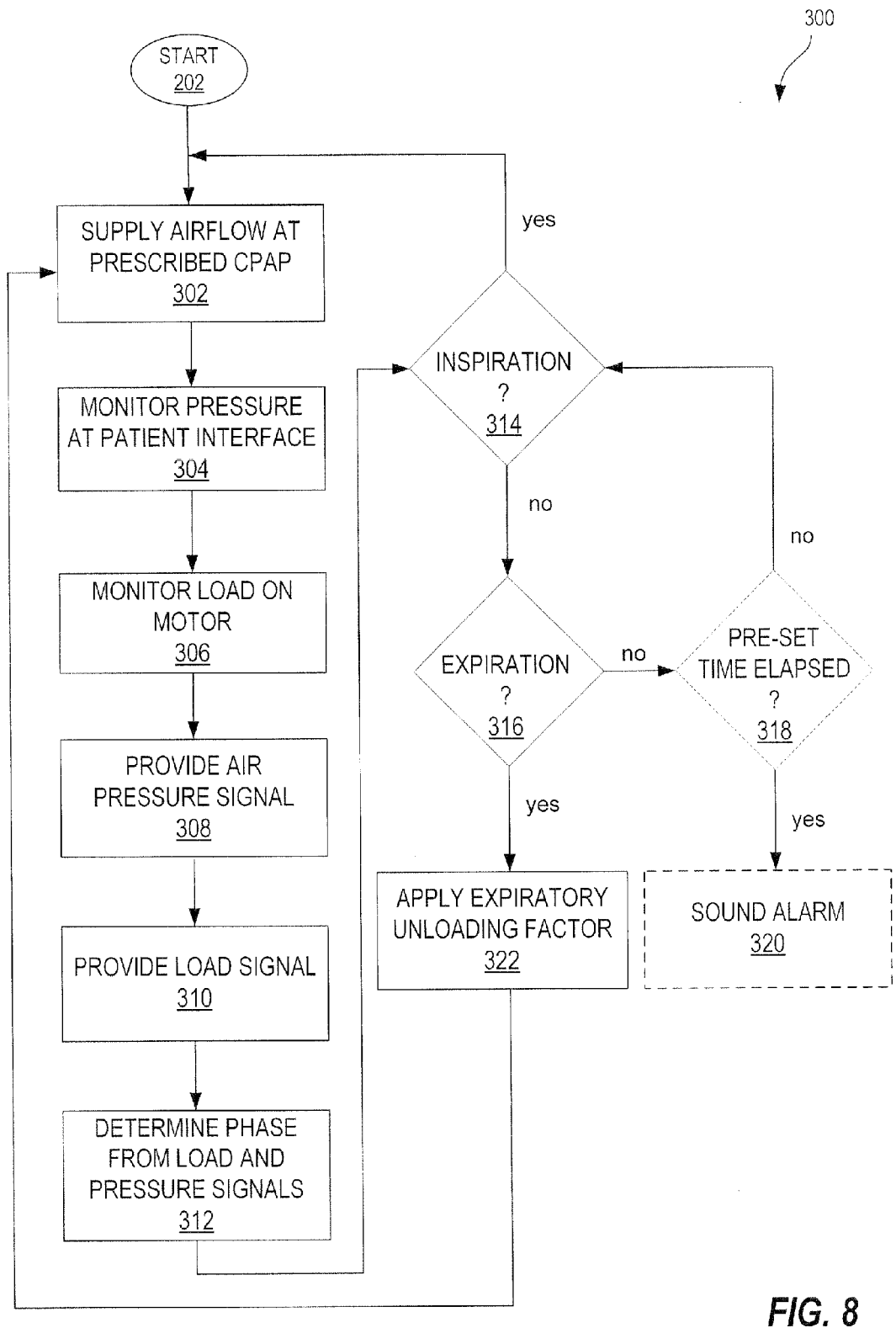
FIG. 8 is a flowchart depicting application of an expiratory unloading factor in a method for providing positive airway pressure to a patient, according to one embodiment.

FIG. 8 is a flowchart illustrating one method 300 for providing positive airway pressure to a patient. Method 300 is for example implemented by apparatus 100, which may be calibrated as described with respect to FIG. 7. Airflow is provided to a patient at prescribed CPAP, in step 302. Air pressure at the patient interface and load upon a flow generator, e.g., motor 110, are measured in steps 304, 306, and air pressure and load signals are provided to decision circuitry in steps 308, 310. In step 312, respiratory phase is determined based upon the pressure and load signals. In one example of steps 302-310, flow generator 106 and more specifically motor 110 and blower 108, provide airflow to patient 102, via connected tubing 114 and patient interface 104. Pressure to the patient is controlled by pressure controller 136 according to output from decision processor 124. Pressure controller 136 for example controls the speed of motor 110 to generate prescribed CPAP, as determined in calibration process 200. Pressure sensor 118 monitors pressure at pressure pickup port 120 and relays pressure signals to decision processor 124. Load sensor 128 monitors load on motor 110 and relays load signals to decision processor 124. Likewise, respiratory phase detector 130 receives load and pressure signals from sensors 128, 118. Respiratory phase detector 130 determines phase of breathing based upon the load and pressure signals, and sends a phase signal to decision processor 124.

Step 314 is a decision. If the phase signal indicates an inspiratory phase (i.e., the patient is inhaling), airflow continues to be supplied at the prescribed CPAP, according to step 302. If the patient is not inhaling, a determination is made as to whether the patient is in an expiratory phase (exhaling), in decision 316. Steps 318, 320 are optional and may, for example, be incorporated where method 300 is applied to an ICU ventilator. If the patient is not inhaling or exhaling, and if a pre-set amount of time has passed, according to decision 318, an alarm may be triggered in step 320, to alert a family member or medical practitioner to the patient's lack of respiration.

If in decision 316 it is determined that the patient is in an expiratory phase, an expiratory unloading factor (EUF) is applied to reduce pressure at the patient interface, in step 322. Expiratory unloading, described further with respect to FIGS. 9, 12 and 13, refers to reduction in motor speed and a corresponding reduction in air pressure provided to a patient during an expiratory phase of respiration. During expiration, pressure is decreased in relation to the change in motor loading.

Figure 9:
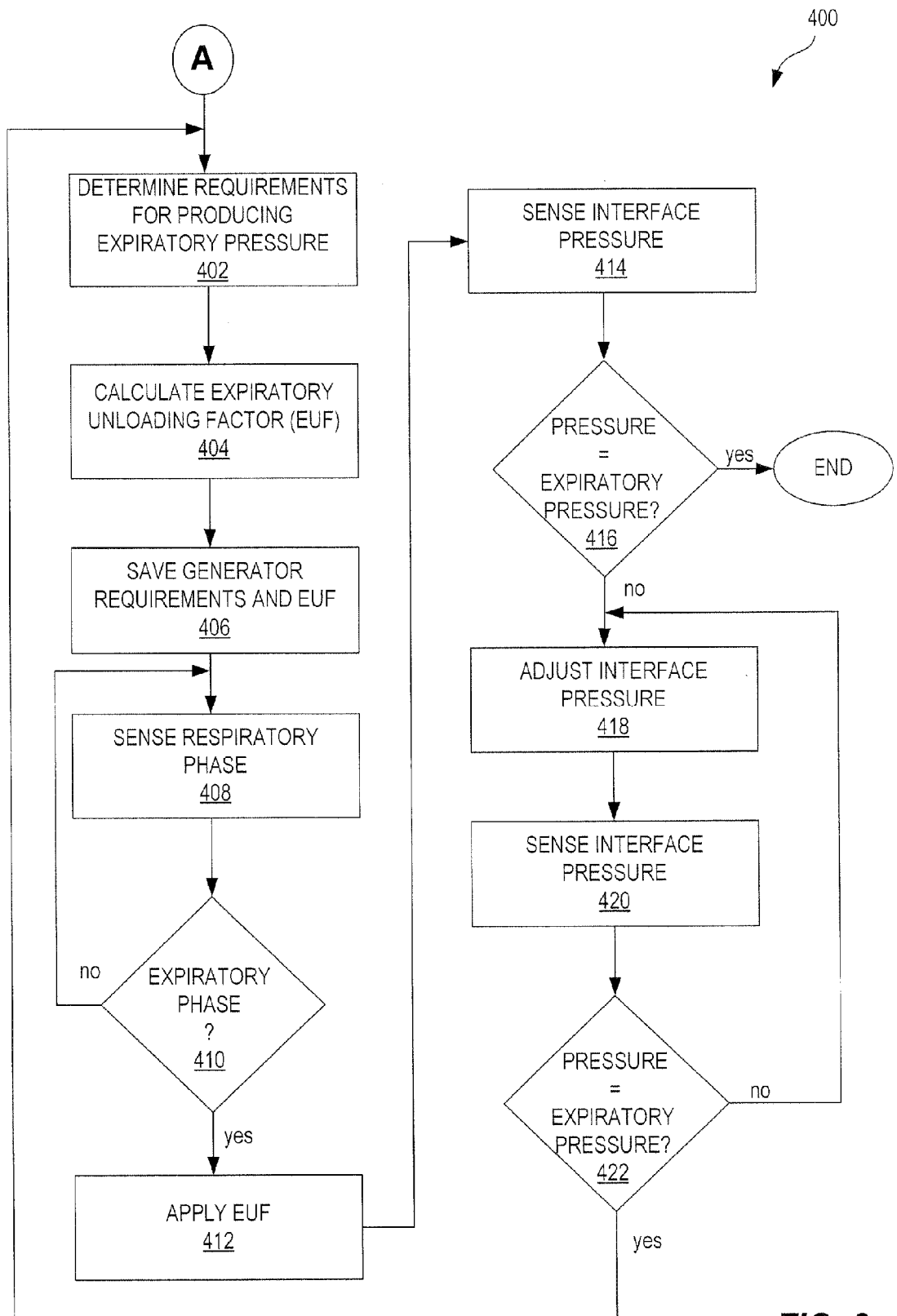
FIG. 9 is a flowchart illustrating determination of an expiratory unloading factor, for application in the method of FIG. 8.

FIG. 9 is a flowchart illustrating a method 400 for determining an expiratory unloading factor. Method 400 branches from calibration method 200, as indicated. In particular, step 402 of FIG. 9 follows step 214 of FIG. 7; thus, the two figures may best be understood when viewed together.

Flow generator or motor requirements for producing a therapeutic expiratory pressure at the patient interface are determined, in step 402. For example, circuitry 124 processes the correlated pressure, load and phase information from step 214 with a desired expiratory pressure measurement, e.g., 4 cm $H_2O$, to determine a motor speed necessary to deliver 4 cm $H_2O$ of air to the patient. In step 404, the EUF is calculated based upon the motor requirements for achieving the desired expiratory pressure and the motor requirements for achieving the CMP, as determined in step 204, FIG. 7. The EUF may be calculated as a percentage or proportional reduction in motor load, where the expiratory pressure is less than the CMP.

In step 406, flow generator or motor requirements determined in step 402, and the EUF determined in step 404, are saved to a memory. In one example of step 406, these requirements are saved to memory 138 of apparatus 100 (FIG. 6). Respiratory phase is sensed in step 408 and, if the phase is expiratory (decision 410), the calculated EUF is applied in step 412. In one example of steps 408-412, respiratory phase detector 130 determines, from input of pressure sensor 118 and load sensor 128, whether patient 102 is inspiring or expiring. If the patient is expiring, decision processor 124 accesses the EUF from memory 138 and signals pressure controller 136 to reduce motor speed by the EUF (e.g., by 40%), to achieve the prescribed expiratory pressure.

Interface pressure is then sensed, in step 414. If the interface pressure is equal to the prescribed expiratory pressure, decision 416, the EUF is correctly calculated and method 400 ends. Method 400 may be a stand alone method for determining the EUF and storing the EUF in memory, or method 500 (described below) may commence once the EUF is correctly calculated.

Returning to decision 416, if interface pressure does not equal the prescribed expiratory pressure, interface pressure is gradually adjusted and sensed, in steps 418, 420. If the prescribed expiratory and interface pressures are equal, decision 422, the requirements for producing the prescribed expiratory pressure are determined, a new EUF is calculated and the requirements and EUF are saved, in steps 402-406. The new EUF is applied and tested as described above, with respect to steps 408-422. In one embodiment, steps 408-422 represent a sampling cycle that is performed at real-time intervals, for example, every 10 ms.

In one example of steps 414-422, pressure sensor 118 senses pressure at pressure pickup port 120, and sends signals indicative of pressure to respiratory phase detector 130 and decision processor 124 (FIG. 6). If the sensed pressure is not equal to the prescribed expiratory pressure, apparatus 100 gradually adjusts pressure by controlling speed of motor 110, and senses pressure changes during this adjustment, with pressure sensor 118. Once the sensed pressure equals the prescribed expiratory pressure, load on motor 110 (e.g., motor speed) necessary to achieve the prescribed expiratory pressure (at patient interface 104) is saved in memory 138, and a new EUF is calculated.

Figure 10:
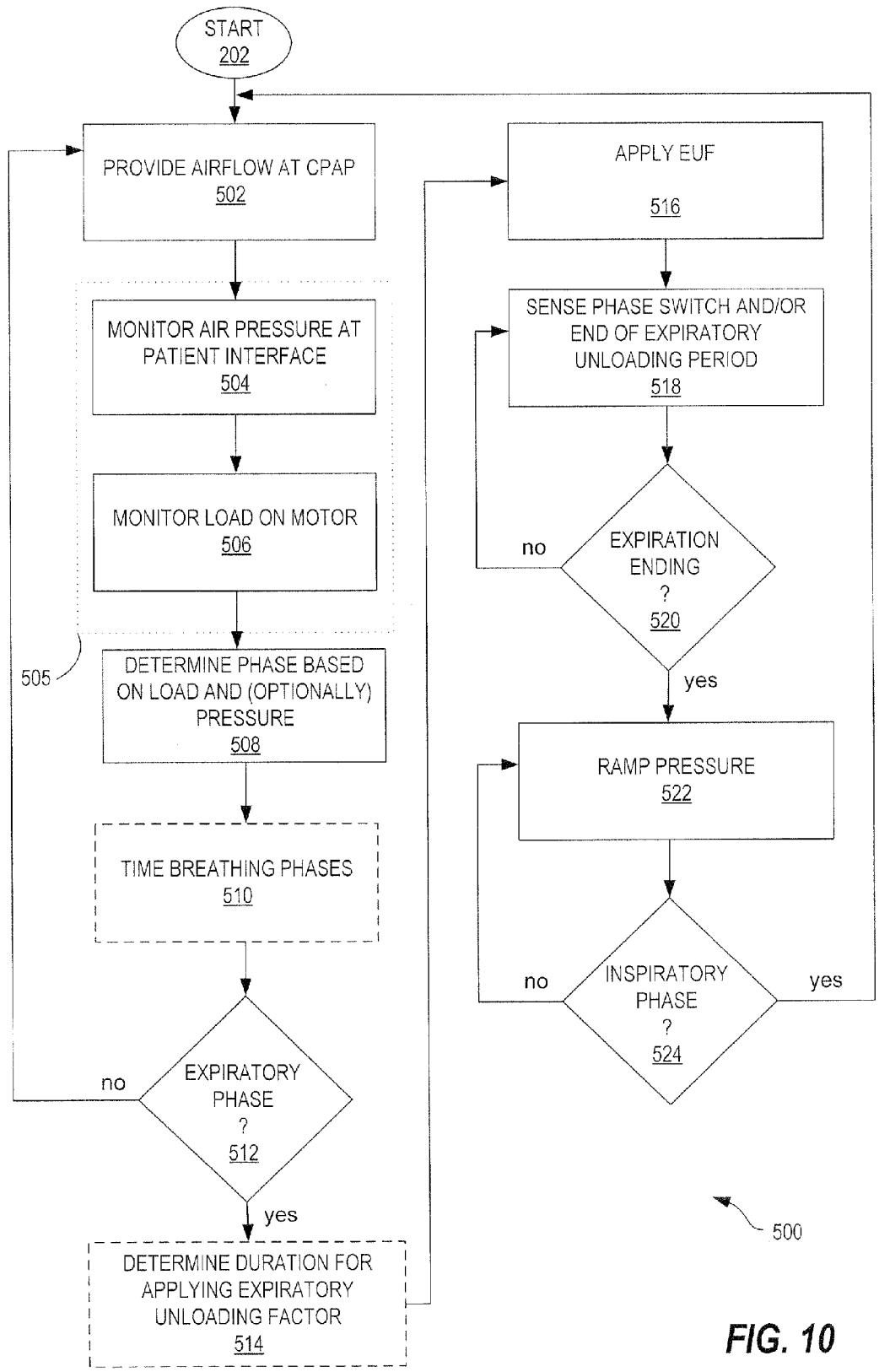
FIG. 10 is a flowchart showing a method for providing positive airway pressure to a patient, according to one embodiment.

FIG. 10 is a flowchart showing a method 500 for providing positive airway pressure to a patient, for example using apparatus 100 calibrated as described with respect to FIGS. 7 and 9. Method 500 is for example implemented, at least in part, by processor 124, FIG. 6. In step 502, airflow is supplied to a patient at a prescribed CPAP level. Pressure at the patient interface and load upon a motor for providing air to the patient are sensed, in steps 504, 506. Steps 504, 506 may be performed more or less simultaneously, as one sensing step indicated by dotted box 505. Where load and pressure parameters have been correlated, e.g., as described above with respect to FIGS. 7-9, respiratory phase may be determined based solely upon measured motor load information, in step 508. Optionally, both motor load information and pressure information may be used to determine respiratory phase. Step 510 is optional. If desired, breathing phases may be timed and timing data stored in a memory. For example, phases may be determined from load and/or pressure information obtained in steps 504, 506, and saved to memory 138 of apparatus 100.

Step 512 is a decision. If the phase is not expiratory, delivery of prescribed CPAP continues in step 502. If the phase is expiratory, duration for applying an EUF may be determined, at optional step 514. In one example of step 514, timer 129 times the duration of a motor load and/or patient interface pressure (or a range thereof) associated with expiration, and calculates an amount or percentage of the total expiratory period to which the EUF should be applied. The EUF may be applied for the first 40 percent of expiration, after which patient interface pressure is increased or ramped to the prescribed CPAP level, as described further below. The determined EUF is applied, in step 516.

In step 518, motor load and/or patient breathing (e.g., pressure) are monitored to detect a switch in respiratory phase. As expiration ends, decision 520, pressure is gradually ramped up toward prescribed CPAP, in step 522, so that prescribed CPAP is provided when inspiration begins, decision 524. Ramping patterns may be determined by a patient's physician, according to comfort or health requirements. Steps 502-524 may continue until a programmed end time, for example when the patient awakes. The end time may be governed by timer 129.

In one example of steps 516-524, an EUF is provided that reduces air pressure during expiration to 40% of the prescribed CPAP. The EUF is for example calculated in step 404, FIG. 9. Based upon an average expiratory phase determination (e.g., determined by timing and recording a number of expiratory phases in steps 510-514, FIG. 5) the EUF is applied for 30% of an average expiratory phase. During the next 70% of the expiratory phase, expiratory unloading is reduced (and air pressure delivered to the patient is increased to CPAP) in proportion with motor load.

In one example of steps 518-524, apparatus 100 (FIG. 6) monitors changes in motor load during patient respiratory cycles. Memory 138 for example includes a range of load values associated with inspiration and a range of load values associated with expiration, determined during calibration (see, e.g., FIGS. 7-9). As patient 102 exhales, load requirements on motor 110 may decrease. Decision processor 124 registers the decrease in load and signals pressure controller 136 to decrease motor speed accordingly, to deliver decreasing pressure to patient interface 104. As patient 102 inhales, load sensor 128 senses a motor load associated (e.g., in memory 138) with inspiration and decision circuitry signals pressure controller 136 to increase motor speed until the pressure at interface 104 reaches the prescribed CPAP. Conversely, as inhalation ends, load sensor 128 registers a load value associated with the end of inspiration and an expiratory unloading factor is applied to decrease motor speed and accordingly decrease pressure at patient interface 104.

Figure 11:
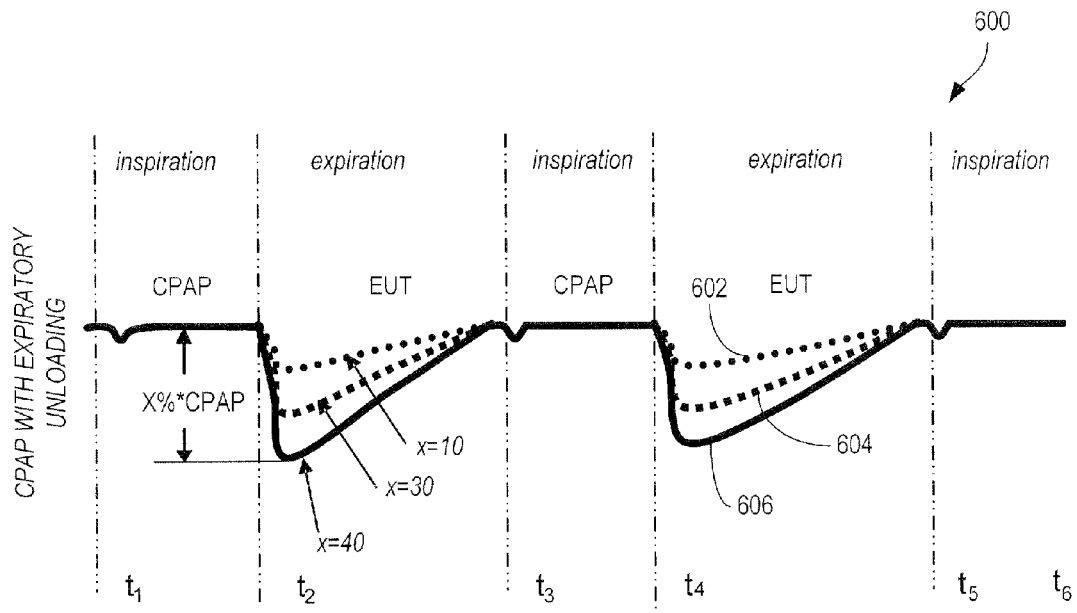
FIG. 11 is a graph of pressure waveforms for CPAP with expiratory unloading as a percentage of CPAP, according to one embodiment.

FIG. 11 is a graphical representation 600 of pressure waveforms for CPAP with expiratory unloading as a percentage of prescribed CPAP. Inspiratory pressure is stabilized by compensating for increased motor load by increasing motor speed during the inspiratory phase. During expiration, pressure is decreased by an expiratory unloading factor, x, in relation to the change in motor loading. A fixed maximum expiratory unloading pressure $P_{EUT\_max}$ may be determined by:

$$P_{EUT\_max} = (1-x)*P_{CPAP} \qquad \text{Eq. 1,}$$

where x is a percentage of applied CPAP level, $P_{CPAP}$. FIG. 11 shows waveforms 602, 604 and 606, corresponding to respective x values of 10%, 30% and 40% of $P_{CPAP}$. $P_{EUT\_max}$ may be a pre-determined number, for example, 3 cm H2O below the CPAP.

The fixed maximum expiratory unloading pressure, $P_{EUT\_max}$, e.g., 10% of the applied CPAP, is attained at the beginning of an expiratory phase and gradually ramped back to the CPAP for the start of an inspiratory phase. In one embodiment, the expiratory unloading pressure is maintained for a period of time equal to about 30% of the average expiratory time of the four preceding expiratory cycles before pressure ramping begins. The pressure rises to $P_{CPAP}$ immediately every time an inspiration phase is detected. The maximum unloading pressure may be input in the form of an expiratory unloading factor, such as a percentage of the desired inspiratory pressure, to expiratory pressure control 124. Processor 124 may use programmed parameters such as motor load (e.g., FIG. 9, steps 402-406) and timing of respiratory cycles (FIG. 10, step 510) to direct pressure controller 136 to regulate the speed of motor 110.

Figure 12:
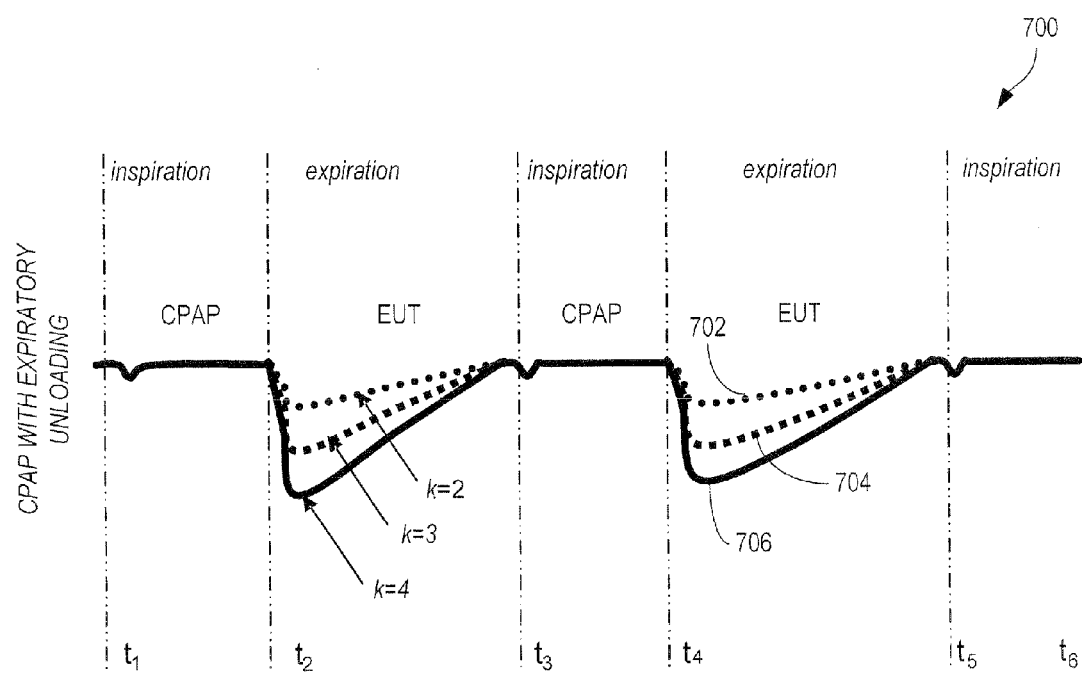
FIG. 12 is a graph of pressure waveforms for CPAP with expiratory unloading proportional to a motor loading factor, according to one embodiment.

FIG. 12 is a graphical representation 700 of pressure waveforms for CPAP with expiratory unloading proportional to a motor loading factor. During expiration, pressure is decreased in relation to the change in motor loading. The pressure at the maximum expiratory unloading point is not fixed. The shape of the pressure waveform during expiratory phases ($t_2$-$t_3$ and $t_4$-$t_5$) reflects motor loading signal line 52, FIG. 3. The actual pressure is determined by an expiratory unloading factor in the form of a gain factor, k. The larger the gain, the more expiratory unloading:

$$P_{EUT}(t) = P_{CPAP} + k*M(t) \qquad \text{Eq. 2}$$

where M(t) is a normalized motor loading factor with 0 as no loading (e.g. at the end of expiratory or start of the next inspiratory phase when the flow is close to zero), −1 as minimum loading and +1 as maximum loading. Any number of pressure waveforms can be generated by varying gain factor k. FIG. 12 shows waveforms 702, 704, 706, for k equal to 2, 3 and 4, respectively.

Figure 13:
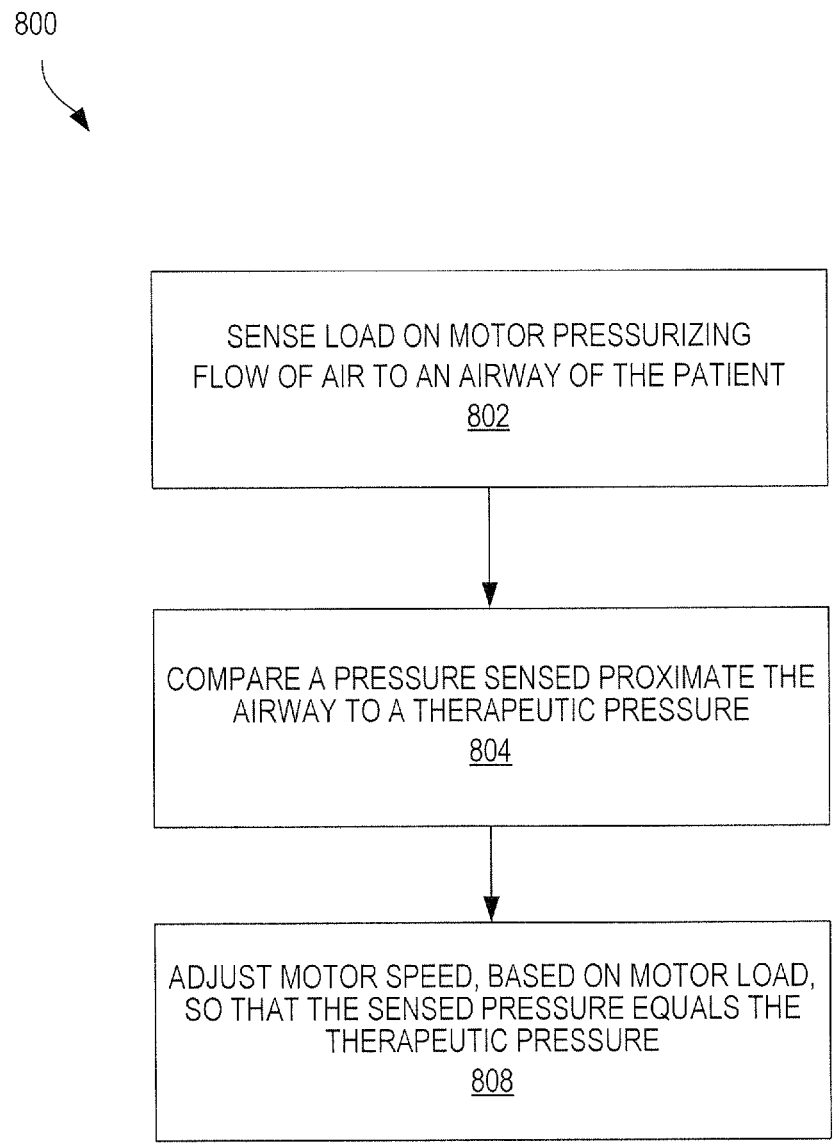
FIG. 13 is a flowchart showing a method for providing positive airway pressure to a patient, according to one embodiment.

FIG. 13 is a flowchart illustrating a method 800 for providing positive airway pressure to a patient. The steps of FIG. 13 are for example implemented by processor 124, FIG. 6.

Load on a motor pressurizing a flow of air to an airway of a patient is sensed, in step 802. In one example of step 802, load sensor 128 (FIG. 6) senses load on motor 110 of flow generator 106, and communicates sensed load to processor 124. In step 804, a pressure sensed proximate the airway is compared with a therapeutic pressure, such as a prescribed CPAP or the inspiratory pressure prescribed for bi-level PAP treatment. Motor speed is adjusted, based upon motor load, so that the sensed pressure equals the therapeutic pressure, in step 806. In one example of steps 804, 806, processor 124 receives a signal indicative of pressure sensed at pressure pickup port 120, from pressure sensor 118. Processor 124 compares the sensed pressure to a therapeutic pressure input via CPAP control 132 and directs pressure controller 136 to increase speed of motor 110, to increase pressure at pickup port 120. Pressure controller 136 may increase pressure (via motor 110) at pickup port 120 until pressure sensed by sensor 118 and the therapeutic pressure are equal. For example, processor 124 may signal controller 136 to stop increasing and/or hold pressure, upon determining that therapeutic and sensed pressures are equal.

Figure 14:
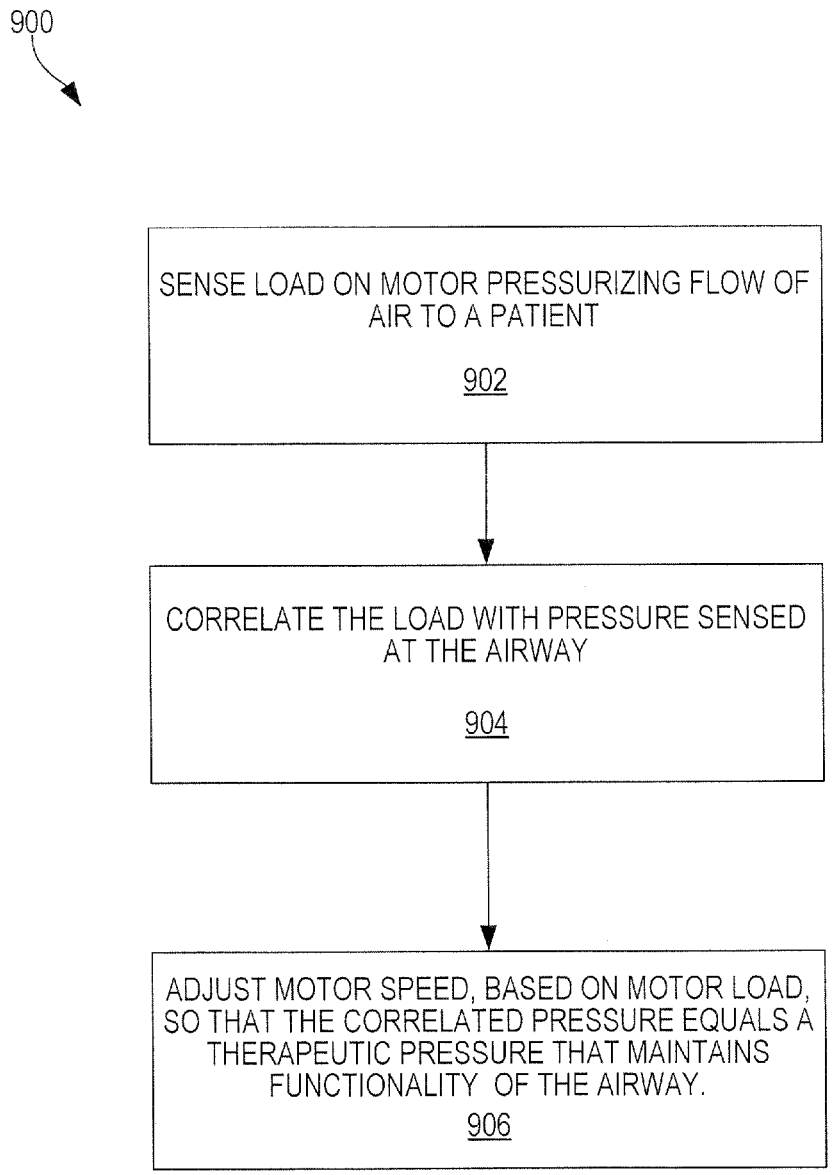
FIG. 14 is a flowchart showing a method for providing positive airway pressure to a patient, according to one embodiment.

FIG. 14 is a flowchart showing a method 900 for providing positive airway pressure to a patient. The steps of FIG. 14 are for example implemented by processor 124, FIG. 6. In step 902, load on a motor pressurizing a flow of air to a patient is sensed. For example, load sensor 128 (FIG. 6) senses load on motor 110 of flow generator 106, and communicates sensed load to processor 124. Motor 110 may operate with blower 108 to deliver the flow of pressurized air to patient 102, via tubing 114 and interface 104. The sensed load is correlated with a pressure sensed at the airway of the patient, in step 904. In one example of step 904, pressure sensor 118 senses air pressure at pickup port 120 and communicates a signal representative of the pressure to processor 124. Processor 124 correlates the pressure with the load communicated by load sensor 128.

In step 906, motor speed is adjusted, based upon motor load, so that the correlated pressure equals a therapeutic pressure that maintains functionality of the airway. In one example of step 906, processor 124 directs pressure controller 136 to adjust speed of motor 110 until pressure sensed by sensor 118 is equal to either a therapeutic pressure input by CPAP control 132, or to a therapeutic expiratory pressure. Processor 124 directs controller 132 to speed motor 110 up when motor load is high, for example during inspiration, to achieve a therapeutic inspiratory pressure/prescribed CPAP level. Processor 124 may also direct controller 132 to slow motor 110 down when motor load is low, for example during expiration, to achieve an expiratory pressure selected for patient comfort. Pressure controller 136 may adjust pressure (by adjusting speed of motor 110) at pickup port 120 until pressure sensed by sensor 118 and the therapeutic CPAP or expiratory pressure are equal.

Changes may be made in the apparatus and methods described herein without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. Apparatus for providing positive airway pressure to a patient, comprising:
   a positive airway pressure module in communication with a CPAP machine, for regulating pressure of air delivered to a patient during an expiratory phase of breathing; wherein
   the module determines load on a CPAP machine motor and correlates the load with a therapeutic CPAP level delivered to the patient, by the CPAP machine; and wherein
   based upon the correlated load and a selected expiratory pressure, the module controls motor speed of the CPAP machine motor to reduce the CPAP level delivered to the patient during the expiratory phase, to the expiratory pressure.

2. The apparatus of claim 1, the module comprising a respiratory phase detector for detecting the expiratory phase; wherein reducing the CPAP level during the expiratory phase comprises reducing the motor speed in proportion to a difference between the inspiratory pressure and the expiratory pressure.

3. The apparatus of claim 1, the module comprising a processor for correlating the load and pressure and processing the correlated load and pressure with the selected expiratory pressure to generate an expiratory unloading factor; wherein the module controls the motor speed by applying the expiratory unloading factor at commencement of the expiratory phase.

4. The apparatus of claim 2, the module communicating with a pressure sensor at a patient interface to determine air pressure delivered at the interface; the module reducing CPAP level according to sensed pressure and motor load, to compensate for changes in: (a) resistive load, related to air pressure as sensed by the pressure sensor, and (b) elastic load, related to patient lung volume and indicated by changes in motor load.

5. Apparatus for providing positive airway pressure to a patient, comprising:
   a positive airway pressure module in communication with a CPAP machine, for regulating pressure of air delivered to a patient during an expiratory phase of breathing, the module including:
   a pressure sensor for monitoring air pressure proximate a patient interface;
   a load sensor for sensing load on a motor of the CPAP machine;
   a respiratory phase detector for detecting inspiration and expiration;
   a processor for receiving and processing information from the pressure sensor, load sensor and expiratory phase detector;
   wherein the processor communicates with the motor of the CPAP machine, determines load on the motor of the CPAP machine and correlates the load with a therapeutic CPAP level delivered to the patient, and
   wherein, based upon the correlated load, pressure sensed at the patient interface and a selected expiratory pressure, the module controls the motor's speed to reduce the CPAP level delivered to the patient during the expiratory phase to the selected expiratory pressure.

6. The apparatus of claim 5, wherein the processor communicates with the motor to reduce motor speed in proportion to a difference between an inspiratory pressure and the selected expiratory pressure.

7. The apparatus of claim 5, the processor processing the correlated load and therapeutic CPAP level with the selected expiratory pressure to generate an expiratory unloading factor; wherein the module controls motor speed by unloading the motor according to the expiratory unloading factor, at commencement of the expiratory phase.

* * * * *